United States Patent [19]

Hazato et al.

[11] Patent Number: 5,656,663
[45] Date of Patent: Aug. 12, 1997

[54] EXTERNAL SKIN TREATMENT AGENT COMPOSITION CONTAINING ISOCARBACYCLINS AS ACTIVE INGREDIENT

[75] Inventors: Atsuo Hazato; Nobuaki Hanajima; Yuji Makino, all of Hino; Toshiaki Takeda, Narashino; Tamotsu Koyama, Hachioji; Takehisa Hata, Nagaokakyo; Sumihisa Kimura, Kawanishi; Saburo Murata, Takarazuka, all of Japan

[73] Assignee: Teijin Limited, Osaka, Japan

[21] Appl. No.: 313,146

[22] PCT Filed: Feb. 3, 1994

[86] PCT No.: PCT/JP94/00163

§ 371 Date: Dec. 28, 1994

§ 102(e) Date: Dec. 28, 1994

[87] PCT Pub. No.: WO94/17805

PCT Pub. Date: Aug. 18, 1994

[30] Foreign Application Priority Data

Feb. 3, 1993 [JP] Japan ................. 5-037280

[51] Int. Cl.$^6$ ................................. A61K 31/215
[52] U.S. Cl. ................ 514/530; 514/824; 514/925; 514/928
[58] Field of Search ................... 514/530, 824, 514/925, 928

[56] References Cited

U.S. PATENT DOCUMENTS

| 4,254,145 | 3/1981 | Birnbaum ................ 514/530 |
| 5,219,885 | 6/1993 | Frölich et al. ............. 514/530 |

FOREIGN PATENT DOCUMENTS

| 0015658 | 9/1980 | European Pat. Off. |
| A13704825 | 8/1988 | Germany. |
| 4164034 | 6/1992 | Japan. |

OTHER PUBLICATIONS

"Recent clinical studies on lipo–PGE$_1$ and lipo–PGE$_2$; PGE$_1$ and PGE$_2$ incorporated in lipid microspheres, for targeted delivery," *Journal of Controlled Release*, vol. 28, 1994 pp. 243–249.

Japan Abstracts 61-197518 (A) "Medicine for circulatory organ containing prostacycline compound as active component" (1985).

*Primary Examiner*—Kevin E. Weddington
*Attorney, Agent, or Firm*—Sughrue, Mion, Zinn, Macpeak & Seas

[57] ABSTRACT

An external skin treatment agent composition containing an active ingredient comprising a prostacyclin, and/or its optical isomer, having the formula (I):

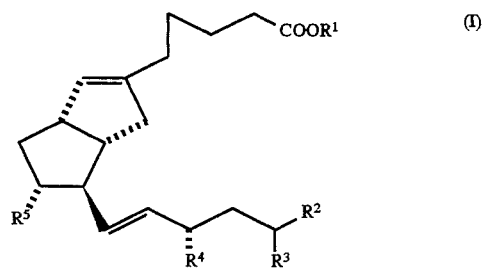

(wherein, $R^1$ is a hydrogen atom, a straight chain or branched alkyl group of $C_1$ to $C_{10}$, or one equivalent of a cation, $R^2$ is a substitutable $C_1$ to $C_{10}$ straight chain or branched alkyl group or substitutable $C_1$ to $C_{10}$ straight chain or branched alkenyl group or alkinyl group, $R^3$ is a straight chain alkyl group of $C_1$ to $C_5$, and $R^4$ and $R^5$ are independently a hydroxyl group or formula:

$$-\underset{\underset{O}{\|}}{O}CR^6$$

(where, $R^6$ is a $C_1$ to $C_5$ straight chain or branched alkyl group)) and a carrier.

5 Claims, 2 Drawing Sheets

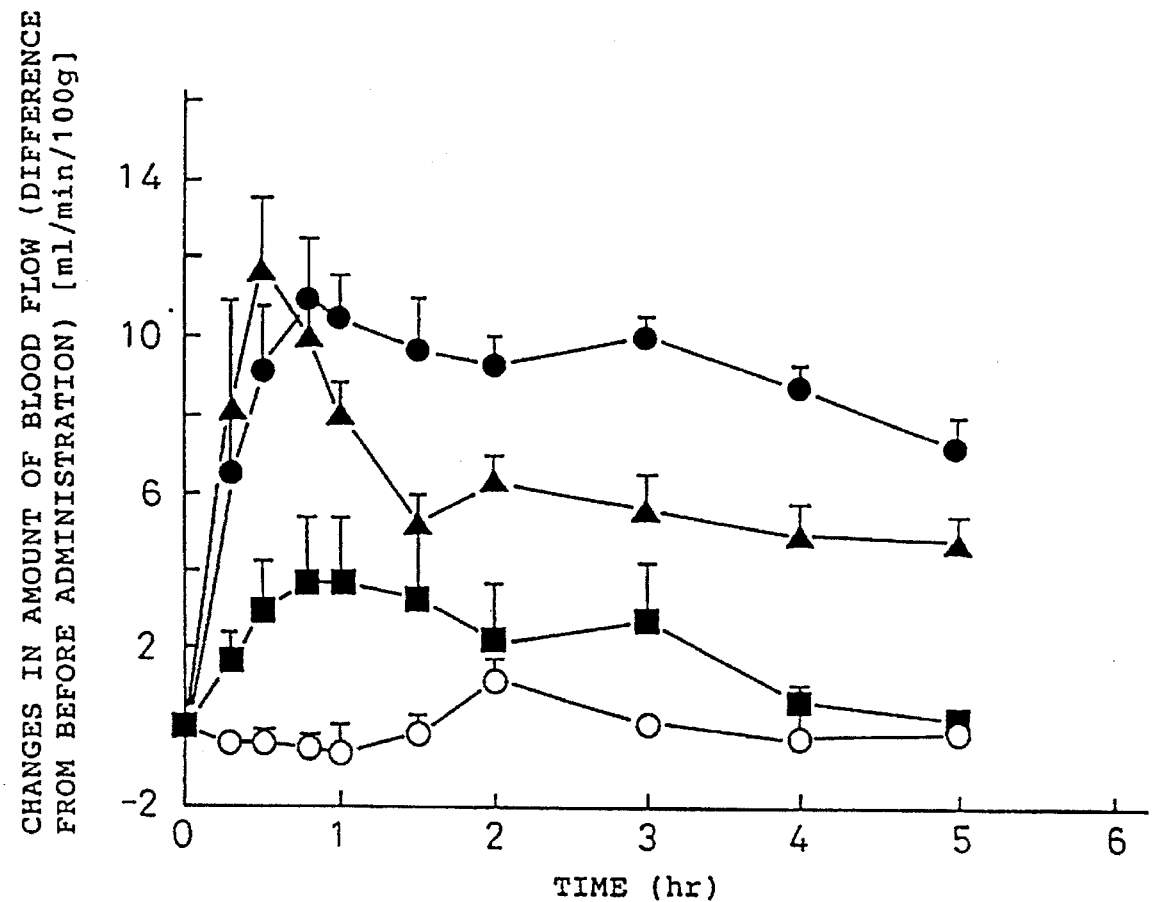

EXTERNAL SKIN TREATMENT AGENT COMPOSITION CONTAINING ISOCARBACYCLINS AS ACTIVE INGREDIENT

DESCRIPTION

This application is 371 of PCT/JP94/00163 filed Feb. 3, 1994.

1. Technical Field

The present invention relates to an external skin treatment agent composition such as an agent for treatment of skin ulcers. More specifically it relates to an external skin treatment agent composition containing an isocarbacyclin derivative as an active ingredient.

2. Background Art

Prostaglandins are compounds which have diverse physiological actions such as a powerful action in suppressing blood platelet aggregation, action in reducing the vasodilation blood pressure, action in suppressing gastric acid secretion, smooth muscle contraction action, cell protection action, and diuretic action and is useful for the treatment or prevention of myocardial infarct, cardiac angina, arteriosclerosis, hypertension, duodenal ulcers, induced parturition, abortion, etc.

On the other hand, in recent years, there has been a tendency toward an increase of skin ulcers, in particular, the decubitus ulcers known commonly as bedsores, along with the higher age of the subjects being treated for various ailments. For example, about 5% of the approximately 12 million senior citizens in Japan today, or 600,000 people, are bed-ridden. These people are said to suffer from decubitus ulcers at a high frequency. In the past, the treatment for skin ulcers, including decubitus ulcers, consisted of improvement of local conditions using antibiotics, antibacterial agents, ointments containing enzymes etc., skin cleaning solutions, or water absorbing polymer powders, wound covering agents, etc. These have been tried along with removal and mitigation of the pressure on the diseased sites, surgical debridement for removal of the destroyed tissue, treatment of systemic conditions by transfusions, intraintestinal nutrition, and IVH, but these treatments still cannot be said to be sufficiently effective. On the other hand, attempts have been made to apply prostaglandins E, prostaglandins F, and prostaglandins $I_1$ transdermal preparations to skin ulcers, including decubitus ulcers, for the purpose of improvement of skin ulcers by application to local areas, but the stability of the main medication, the release of the main medication from the ointment, the stimulus to the skin, and the efficacy have not always necessarily met clinical requirements.

Natural prostacyclin, however, is a local hormone produced mainly by the hemangioendothelium in the body. Attempts have been made to make use of its powerful physiological activity, for example, its activity in suppressing aggregation of blood platelets, its vasodilation activity, etc. to use the same as a direct pharmaceutical (P. J. Lewis, J. O. Grady, Clinical Pharmacology of Prostaglandin). Natural prostacyclin, however, contains an enol ether bond which is extremely easily hydrolyzed in the molecules, and therefore, easily loses its activity under neutral or acidic conditions. Accordingly, it cannot be said to be a desirable compound as a pharmaceutical due to its chemical instability. Therefore, intensive research has been carried out on synthesizing a synthetic prostacyclin which has a similar physiological activity as natural prostacyclin and is chemically stable (Synthesis, 1984, 449). The present inventors succeeded in synthesizing the prostacyclin analogs, which are 9(O)-methano-$\Delta^{6(9\alpha)}$-protaglandin $I_2$ (isocarbacyclin) derivatives, which are sufficiently satisfactory in the chemical stability, by replacing oxygen atoms at the 6(9$\alpha$)-position of prostacyclin with the methine group (—CH=) (see Japanese Unexamined Patent Publication (Kokai) No. 59-210044). This derivative has physiological activity, such as a powerful action in inhibitory effect on aggregation of blood platelets and an action in reducing the blood pressure, comparable with natural prostacyclin and is useful for cardiovascular system (see Japanese Unexamined Patent Publication (Kokai) Nos. 59-210044 and 61-197518).

DISCLOSURE OF THE INVENTION

The present inventors took note of the powerful activity in suppressing aggregation of blood platelets and vasodilation action of stabilized prostacyclin derivatives (isocarbacyclins) and engaged in intensive studies on the possibilities of it as an external skin treatment agent such as an agent for treatment of skin ulcers, including decubitus ulcers, and as a result, found activity suggesting that possibility in isocarbacyclin in the present invention and thereby reached the present invention.

That is, in accordance with the present invention, there is provided an external skin treatment agent composition containing an active ingredient comprising an isocarbacyclin, and/or its optical isomer, having the formula (I):

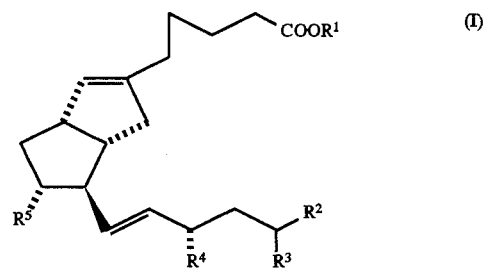

(wherein, $R^1$ is a hydrogen atom, a straight chain or branched alkyl group of $C_1$ to $C_{10}$, or one equivalent of a cation, $R^2$ is a substitutable $C_1$ to $C_{10}$ straight chain or branched alkyl group or substitutable $C_2$ to $C_{10}$ straight chain or branched alkenyl group or alkynyl group, $R^3$ is a straight chain alkyl group of $C_1$ to $C_5$, and $R^4$ and $R^5$ are independently a hydroxyl group or formula:

(wherein, $R^6$ is a $C_1$ to $C_5$ straight chain or branched alkyl group)) and a carrier.

BRIEF DESCRIPTION OF THE DRAWINGS

FIG. 3 is a graph of the by the external skin treatment agent composition of the present invention (Three concentrations) (hairless rats). Dosage: 23 mg/4.5 cm².

Figure 1:
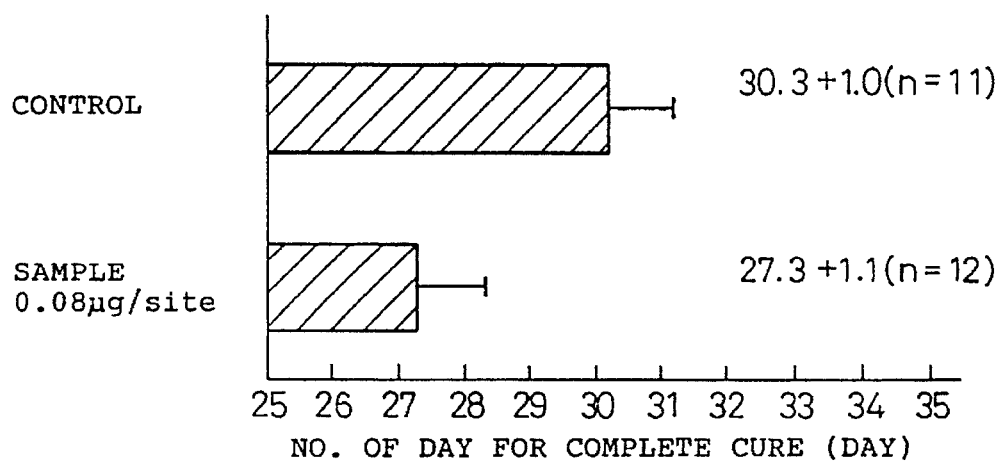
FIG. 1 is a graph of the results of an evaluation of the pharmacological effect of sample ointment of an external skin treatment agent composition of the present invention by a rat scalding model (No. of days for complete cure, n=11 to 12, Average ±SE)

Treated Portion: Thigh (Depilated, Open System). Blood Flowmeter: Laser Flowmeter (Advance Co., Ltd.).

BEST MODE FOR CARRYING OUT THE INVENTION

In the formula (I), $R^1$ is a hydrogen atom, a $C_1$ to $C_{10}$ straight chain or branched alkyl group, or one equivalent weight of cations. As the $C_1$ to $C_{10}$ alkyl group, mention may be made, for example, of a methyl group, ethyl group, n-propyl group, iso-propyl group, n-butyl group, sec-butyl group, tert-butyl group, n-pentyl group, n-hexyl group, n-heptyl group, n-octyl group, n-nonyl group, n-decyl group, etc. Among these, a $C_1$ to $C_6$ alkyl group, in particular, a $C_1$ to $C_4$ alkyl group, is preferable. As the one equivalent weight of cations, mention may be made, for example, of alkali metal cations such as $Na^+$, $K^+$, bivalent or trivalent metal cations such as $½Ca^{2+}$, $½Mg^{2+}$, $⅓Al^{3+}$, ammonium cations such as, ammonium ions, tetramethyl ammonium ions. As $R^1$, a hydrogen atom or methyl group is particularly preferred, more particularly a methyl group is preferred.

In formula (I), $R^2$ is a substitutable $C_1$ to $C_{10}$ straight chain or branched alkyl group or substitutable $C_2$ to $C_{10}$ straight chain or branched alkenyl group or alkynyl group. As the unsubstituted $C_1$ to $C_{10}$ alkyl group mention may be made for example of a methyl group, ethyl group, n-propyl group, iso-propyl group, n-butyl group, sec-butyl group, tert-butyl group, n-pentyl group, 2-methylbutyl-4-yl group, 3-methylbutyl-4-yl group, 4-methylbutyl-4-yl group, n-hexyl group, 2-methylpentyl-5-yl group, 3-methylpentyl-5-yl group, 4-methylpentyl-5-yl group, 5-methylpentyl-5-yl group, n-heptyl group, 2-methylhexyl-6-yl group, 3-methylhexyl-6-yl group, 4-methylhexyl-6-yl group, 5-methylhexyl-6-yl group, 6-methylhexyl-6-yl group, etc.

Further, as the unsubstituted $C_2$ to $C_{10}$ alkenyl group of $R^2$ of the formula (I), mention may be made, for example, of a 1-methylvinyl group, vinyl group, 1-propenyl group, 1-butenyl group, 1-pentenyl group, 1-hexenyl group, 1-heptenyl group, allyl group, methallyl group, 2-butenyl group, 2-pentenyl group, 2-hexenyl group, 2-heptenyl group, 1-pentene-2-yl group, 3-methyl-1-butene-1-yl group, 3-methyl-1-pentene-1-yl group, 4-methyl-1-pentene-1-yl group, 3-methyl-1-hexene-1-yl group, 4-methyl-1-hexene-1-yl group, 3-methyl-1-heptene-1-yl group, 5-methyl-1-heptene-1-yl group, 3,3-dimethyl-1-heptene-1-yl group, 2-pentene-3-yl group, 3-methyl-2-butenyl group, 4-methyl-2-pentenyl group, 4-methyl-2-hexenyl group, 5-methyl-2-heptenyl group, 4,4-dimethyl-2-hexenyl group, 1-butene-4-yl group, 2-methyl-1-butene-4-yl group, 3-methyl-1-butene-4-yl group, 2-pentene-4-yl group, 3-hexenyl group, 3-heptenyl group, 3,3-dimethyl-1-butene-4-yl group, 1-pentene-5-yl group, 4-methyl-pentene-5-yl group, 4,4-dimethyl-pentene-5-yl group, 3-methyl-pentene-5-yl group, 2-methyl-pentene-5-yl group, 2-hexene-6-yl group, 2-methyl-2-hexene-6-yl group, 5-methyl-2-hexene-6-yl group, 5,5-dimethyl-2-hexene-6-yl group, 4-ethyl-3-hexenyl group, 4-methyl-3-hexenyl group, 2-methyl-2-pentene group, 2-methyl-3-hexenyl group, 5-methyl-3-hexenyl group, 2-methyl-3-heptenyl group, 6-methyl-3-heptenyl group, 2,5-dimethyl-2-hexene-6-yl group, 2-methyl-2-heptene-6-yl group, 2,6-dimethyl-2-heptene-6-yl group, 3-heptene-7-yl group, 3-methyl-heptene-7-yl group, 3-ethyl-heptene-7-yl group, 5-methyl-heptene-7-yl group, 6-methyl-heptene-7-yl group, 6,6-dimethyl-heptene-7-yl group, etc.

Further, as the unsubstituted $C_2$ to $C_{10}$ alkenyl group of $R^2$ of the formula (I), mention may be made, for example, of an ethynyl group, 1-propine-3-yl group, butynyl group, pentynyl group, hexynyl group, heptynyl group, 3-methyl-butynyl group, 3,3-dimethyl-butynyl group, 3-methyl-pentynyl group, 3,3-dimethyl-pentynyl group, 3-ethyl-pentynyl group, 4-methyl-pentynyl group, 4,4-dimethyl-pentynyl group, 3-methyl-hexynyl group, 3,3-dimethyl-hexynyl group, 5-methyl-hexynyl group, 5,5-dimethyl-hexynyl group, 3-methyl-heptynyl group, 3,3-dimethyl-heptynyl group, 5-methyl-heptynyl group, 5-ethyl-heptynyl group, 5,5-dimethyl-heptynyl group, 1-propine-3-yl group, 1-butine-3-yl group, 2-pentine-3-yl group, 2-butine-1-yl group, 2-pentine-1-yl group, 4-methyl-2-pentine-1-yl group, 4,4-dimethyl-2-pentine-1-yl group, 2-hexine-1-yl group, 4-methyl-2-hexine-1-yl group, 4-ethyl-2-hexine-1-yl group, 4,4-dimethyl-2-hexine-1-yl group, 2-heptine-1-yl group, 3-octine-2-yl group, 4-methyl-2-heptine-1-yl group, 4,4-dimethyl-2-heptine-1-yl group, 5,5-dimethyl-2-heptine-1-yl group, 5-ethyl-2-heptine-1-yl group, 3-heptine-2-yl group, 1-butine-4-yl group, 1-pentine-4-yl group, 3-methyl-1-butine-4-yl group, 2-pentine-5-yl group, 3-hexine-1-yl group, 5-methyl-3-hexine-1-yl group, 2-methyl-3-hexine-1-yl group, 5,5-dimethyl-3-hexine-1-yl group, 2,2-dimethyl-3-hexine-1-yl group, 3-heptine-1-yl group, 4-octine-2-yl group, 2-methyl-4-octine-2-yl group, 2,2-dimethyl-3-heptine-1-yl group, 2-methyl-3-heptine-1-yl group, 5-methyl-3-heptine-1-yl group, 2-hexine-5-yl group, 5-ethyl-3-heptine-1-yl group, 6-methyl-3-heptine-1-yl group, 6,6-dimethyl-3-heptine-1-yl group, 1-pentine-5-yl group, 1-hexine-5-yl group, 4-methyl-1-pentine-5-yl group, 4,4-dimethyl-1-pentine-5-yl group, 3-methyl-1-pentine-5-yl group, 3,3-dimethyl-1-pentine-5-yl group, 2-hexine-6-yl group, 2-heptine-6-yl group, 5-methyl-2-hexine-6-yl group, 5,5-dimethyl-2-hexine-6-yl group, 4-methyl-2-hexine-6-yl group, 4,4-dimethyl-2-hexine-6-yl group, 3-heptine-7-yl group, 3-octine-7-yl group, 6-methyl-3-heptine-7-yl group, 6,6-dimethyl-3-heptine-7-yl group, 5-methyl-3-heptine-7-yl group, 2-methyl-3-heptine-7-yl group, 2,2-dimethyl-3-heptine-7-yl group, 1-hexine-6-yl group, 1-heptine-6-yl group, 6-methyl-1-heptine-6-yl group, 5-methyl-1-hexine-6-yl group, 5,5-dimethyl-1-hexine-6-yl group, 4-methyl-1-hexine-6-yl group, 3-methyl-1-hexine-6-yl group, 3,3-dimethyl-1-hexine-6-yl group, 2-heptine-7-yl group, 2-octine-7-yl group, 7-methyl-2-octine-7-yl group, 5,5-dimethyl-2-heptine-7-yl group, 4-methyl-2-heptine-7-yl group, 4,4-dimethyl-2-heptine-7-yl group, 1-heptine-7-yl group, 1-octine-7-yl group, 7-methyl-1-octine-7-yl group, 5-methyl-1-heptine-7-yl group, 4-methyl-1-heptine-7-yl group, 3-methyl-1-heptine-7-yl group, 3,3-dimethyl-1-heptine-7-yl group, 4,4-dimethyl-1-heptine-7-yl group, etc.

As the $R^2$ substituent groups, mention may be made of halogen atoms such as fluorine, chlorine; lower alkoxy groups such as a methoxy group, ethoxy group, propoxy group, butoxy group; $C_3$ to $C_8$ cycloalkyl groups such as cyclopentyl group, cyclohexyl group. Among these, a lower alkoxy group or cycloalkyl group is preferred.

As the $R^2$ in the formula (I), a $C_3$ to $C_5$ alkyl group is preferred, more preferably an n-propel group or n-butyl group, particularly preferably an n-propyl group.

In formula (I), $R^3$ is a $C_1$ to $C_5$ straight chain alkyl group. As an example, mention may be made of a methyl group, ethyl group, n-propyl group, and n-pentyl group. Among these, as $R^3$, a $C_1$ to $C_4$ alkyl group, further, a $C_1$ to $C_3$ alkyl group, in particular a methyl group, is preferred.

In formula (I), further, $R^4$ and $R^5$ are independently, that is, the same or different, a hydroxyl group or the formula:

Here, $R^6$ is a $C_1$ to $C_5$ straight chain or branched alkyl group, for example, mention may be made of ones similar to the examples of $R^2$. As the $R^6$, a $C_1$ to $C_3$ alkyl group is preferable, in particular a straight chain alkyl group. It should be noted that as $R^6$, a methyl group is particularly preferred. Further, as the $R^4$ and $R^5$, a hydroxyl group is particularly preferable.

The isocarbacyclins expressed in formula (I) with configurations of the 8-, 9-, 11-, 12-, and 15-positions the same as natural prostacyclins are a particularly useful stereoisomer, but the present invention includes the stereoisomers resulting from different configurations thereof and any combinations thereof.

The configuration of the alkyl group at the 17-position in the formula (I) may be an S-isomer, R-isomer, or any mixture of the same, but an S-isomer is particularly preferable.

Preferable specific examples of the isocarbacyclins usable in the present invention are as follows:

(1) 17-methyl-9(O)-methano-$\Delta^{6(9\alpha)}$-prostaglandin $I_1$
(2) 17(R),20-dimethyl-9(O)-methano-$\Delta^{6(9\alpha)}$-prostaglandin $I_1$
(3) 17(S),20-dimethyl-9(O)-methano-$\Delta^{6(9\alpha)}$-prostaglandin $I_1$
(4) 20-nol-17-methyl-9(O)-methano-$\Delta^{6(9\alpha)}$-prostaglandin $I_1$
(5) 17,19-dimethyl-9(O)-methano-$\Delta^{6(9\alpha)}$-prostaglandin $I_1$
(6) 17,18-dimethyl-9(O)-methano-$\Delta^{6(9\alpha)}$-prostaglandin $I_1$
(7) 17-methyl-20-ethyl-9(O)-methano-$\Delta^{6(9\alpha)}$-prostaglandin $I_1$
(8) 17-methyl-20-isopropyl-9(O)-methano-$\Delta^{6(9\alpha)}$-prostaglandin $I_1$
(9) 17,20-dimethyl-20-ethyl-9(O)-methano-$\Delta^{6(9\alpha)}$-prostaglandin $I_1$
(10) 17,19-dimethyl-20-ethyl-9(O)-methano-$\Delta^{6(9\alpha)}$-prostaglandin $I_1$
(11) 17,18-dimethyl-20-ethyl-9(O)-methano-$\Delta^{6(9\alpha)}$-prostaglandin $I_1$
(12) 17-methyl-20-propyl-9(O)-methano-$\Delta^{6(9\alpha)}$-prostaglandin $I_1$
(13) 17,22-dimethyl-20-propyl-9(O)-methano-$\Delta^{6(9\alpha)}$-prostaglandin $I_1$
(14) 17,21-dimethyl-20-propyl-9(O)-methano-$\Delta^{6(9\alpha)}$-prostaglandin $I_1$
(15) 17,20-dimethyl-20-propyl-9(O)-methano-$\Delta^{6(9\alpha)}$-prostaglandin $I_1$
(16) 17,19-dimethyl-20-propyl-9(O)-methano-$\Delta^{6(9\alpha)}$-prostaglandin $I_1$
(17) 17,18-dimethyl-20-propyl-9(O)-methano-$\Delta^{6(9\alpha)}$-prostaglandin $I_1$
(18) 20-nol-17-methyl-18-methylene-9(O)-methano-$\Delta^{6(9\alpha)}$-prostaglandin $I_1$
(19) 20-nol-18,19-dehydro-17-methyl-9(O)-methano-$\Delta^{6(9\alpha)}$-prostaglandin $I_1$
(20) 18,19-dehydro-17-methyl-9(O)-methano-$\Delta^{6(9\alpha)}$-prostaglandin $I_1$
(21) 18,19-dehydro-17,20-dimethyl-9(O)-methano-$\Delta^{6(9\alpha)}$-prostaglandin $I_1$
(22) 18,19-dehydro-20-ethyl-17-methyl-9(O)-methano-$\Delta^{6(9\alpha)}$-prostaglandin $I_1$
(23) 18,19-dehydro-20-propyl-17-methyl-9(O)-methano-$\Delta^{6(9\alpha)}$-prostaglandin $I_1$
(24) 18,19-dehydro-20-butyl-17-methyl-9(O)-methano-$\Delta^{6(9\alpha)}$-prostaglandin $I_1$
(25) 18-methylene-17,20-dimethyl-9(O)-methano-$\Delta^{6(9\alpha)}$-prostaglandin $I_1$
(26) 18,19-dehydro-17,20,20-trimethyl-9(O)-methano-$\Delta^{6(9\alpha)}$-prostaglandin $I_1$
(27) 18,19-dehydro-17,20-dimethyl-20-ethyl-9(O)-methano-$\Delta^{6(9\alpha)}$-prostaglandin $I_1$
(28) 18,19-dehydro-20-isopropyl-17-methyl-20-ethyl-9(O)-methano-$\Delta^{6(9\alpha)}$-prostaglandin $I_1$
(29) 18,19-dehydro-17,20-dimethyl-20-butyl-9(O)-methano-$\Delta^{6(9\alpha)}$-prostaglandin $I_1$
(30) 18,19-dehydro-17-methyl-20-(1-methylpropyl)-9(O)-methano-$\Delta^{6(9\alpha)}$-prostaglandin $I_1$
(31) 18,19-dehydro-17,20-dimethyl-20-propyl-9(O)-methano-$\Delta^{6(9\alpha)}$-prostaglandin $I_1$
(32) 18,19-dehydro-17,20,20-trimethyl-20-butyl-9(O)-methano-$\Delta^{6(9\alpha)}$-prostaglandin $I_1$
(33) 19,20-dehydro-17-methyl-9(O)-methano-$\Delta^{6(9\alpha)}$-prostaglandin $I_1$
(34) 19,20-dehydro-17,20-dimethyl-9(O)-methano-$\Delta^{6(9\alpha)}$-prostaglandin $I_1$
(35) 19,20-dehydro-17,19-dimethyl-9(O)-methano-$\Delta^{6(9\alpha)}$-prostaglandin $I_1$
(36) 19,20-dehydro-17-methyl-20-ethyl-9(O)-methano-$\Delta^{6(9\alpha)}$-prostaglandin $I_1$
(37) 19,20-dehydro-17-methyl-20-propyl-9(O)-methano-$\Delta^{6(9\alpha)}$-prostaglandin $I_1$
(38) 19,20-dehydro-17-methyl-20-butyl-9(O)-methano-$\Delta^{6(9\alpha)}$-prostaglandin $I_1$
(39) 19,20-dehydro-17,18,20-trimethyl-9(O)-methano-$\Delta^{6(9\alpha)}$-prostaglandin $I_1$
(40) 19,20-dehydro-17-methyl-20-(1-methylpropyl-9(O)-methano-$\Delta^{6(9\alpha)}$-prostaglandin $I_1$
(41) 19,20-dehydro-17-methyl-20-isopropyl-9(O)-methano-$\Delta^{6(9\alpha)}$-prostaglandin $I_1$
(42) 19,20-dehydro-17-methyl-20-(2-methylbutyl)-9(O)-methano-$\Delta^{6(9\alpha)}$-prostaglandin $I_1$
(43) 19,20-dehydro-17-methyl-20-(1,1-dimethylpropyl)-9(O)-methano-$\Delta^{6(9\alpha)}$-prostaglandin $I_1$
(44) 17-methyl-20-methylene-9(O)-methano-$\Delta^{6(9\alpha)}$-prostaglandin $I_1$
(45) 17,20-dimethyl-20-methylene-9(O)-methano-$\Delta^{6(9\alpha)}$-prostaglandin $I_1$
(46) 17,19-dimethyl-20-methylene-9(O)-methano-$\Delta^{6(9\alpha)}$-prostaglandin $I_1$
(47) 17-methyl-20-ethylidene-9(O)-methano-$\Delta^{6(9\alpha)}$-prostaglandin $I_1$
(48) 17-methyl-20-propylidene-9(O)-methano-$\Delta^{6(9\alpha)}$-prostaglandin $I_1$
(49) 17-methyl-20-butylidene-9(O)-methano-$\Delta^{6(9\alpha)}$-prostaglandin $I_1$
(50) 17-methyl-20-(1-ethylbutylidene)-9(O)-methano-$\Delta^{6(9\alpha)}$-prostaglandin $I_1$
(51) 17-methyl-20-(1-methylbutylidene)-9(O)-methano-$\Delta^{6(9\alpha)}$-prostaglandin $I_1$
(52) 17-methyl-20-(1-methylethylidene)-9(O)-methano-$\Delta^{6(9\alpha)}$-prostaglandin $I_1$
(53) 17,19-dimethyl-20-propylidene-9(O)-methano-$\Delta^{6(9\alpha)}$-prostaglandin $I_1$
(54) 17-methyl-20-(2-methylpropylidene)-9(O)-methano-$\Delta^{6(9\alpha)}$-prostaglandin $I_1$
(55) 17,19-dimethyl-20-butylidene-9(O)-methano-$\Delta^{6(9\alpha)}$-prostaglandin $I_1$
(56) 17-methyl-20-(3-methylbutylidene)-9(O)-methano-$\Delta^{6(9\alpha)}$-prostaglandin $I_1$
(57) 17,19,19-trimethyl-20-methylene-9(O)-methano-$\Delta^{6(9\alpha)}$-prostaglandin $I_1$
(58) 17-methyl-20-vinyl-9(O)-methano-$\Delta^{6(9\alpha)}$-prostaglandin $I_1$

(59) 17,19-dimethyl-20-vinyl-9(O)-methano-$\Delta^{6(9\alpha)}$-prostaglandin $I_1$
(60) 17,19,19-trimethyl-20-vinyl-9(O)-methano-$\Delta^{6(9\alpha)}$-prostaglandin $I_1$
(61) 17,20-dimethyl-20-vinyl-9(O)-methano-$\Delta^{6(9\alpha)}$-prostaglandin $I_1$
(62) 17-methyl-20-(1-methylvinyl)-9(O)-methano-$\Delta^{6(9\alpha)}$-prostaglandin $I_1$
(63) 17-methyl-20-(1-propenyl)-9(O)-methano-$\Delta^{6(9\alpha)}$-prostaglandin $I_1$
(64) 17-methyl-20-(2-methyl-1-propenyl)-9(O)-methano-$\Delta^{6(9\alpha)}$-prostaglandin $I_1$
(65) 17,19-dimethyl-20-(1-propenyl)-9(O)-methano-$\Delta^{6(9\alpha)}$-prostaglandin $I_1$
(66) 17,19,19-trimethyl-20-(1-propenyl)-9(O)-methano-$\Delta^{6(9\alpha)}$-prostaglandin $I_1$
(67) 17,19-dimethyl-20-(2-methyl-1-propenyl)-9(O)-methano-$\Delta^{6(9\alpha)}$-prostaglandin $I_1$
(68) 17,18-dimethyl-20-(2-methyl-1-propenyl)-9(O)-methano-$\Delta^{6(9\alpha)}$-prostaglandin $I_1$
(69) 17,18,18-trimethyl-20-(2-methyl-1-propenyl)-9(O)-methano-$\Delta^{6(9\alpha)}$-prostaglandin $I_1$
(70) 17-methyl-20-(1-butenyl)-9(O)-methano-$\Delta^{6(9\alpha)}$-prostaglandin $I_1$
(71) 17-methyl-20-(2-methyl-1-butenyl)-9(O)-methano-$\Delta^{6(9\alpha)}$-prostaglandin $I_1$
(72) 17-methyl-20-(2-ethyl-1-butenyl)-9(O)-methano-$\Delta^{6(9\alpha)}$-prostaglandin $I_1$
(73) 17,20-dimethyl-20-butenyl-9(O)-methano-$\Delta^{6(9\alpha)}$-prostaglandin $I_1$
(74) 17,19-dimethyl-20-butenyl-9(O)-methano-$\Delta^{6(9\alpha)}$-prostaglandin $I_1$
(75) 17,19,19-trimethyl-20-butenyl-9(O)-methano-$\Delta^{6(9\alpha)}$-prostaglandin $I_1$
(76) 20-nol-18,19-tetrahydro-17-methyl-9(O)-methano-$\Delta^{6(9\alpha)}$-prostaglandin $I_1$
(77) 18,19-tetrahydro-17-methyl-9(O)-methano-$\Delta^{6(9\alpha)}$-prostaglandin $I_1$
(78) 18,19-tetrahydro-17,20-dimethyl-9(O)-methano-$\Delta^{6(9\alpha)}$-prostaglandin $I_1$
(79) 18,19-tetrahydro-17-methyl-20-ethyl-9(O)-methano-$\Delta^{6(9\alpha)}$-prostaglandin $I_1$
(80) 18,19-tetrahydro-17-methyl-20-butyl-9(O)-methano-$\Delta^{6(9\alpha)}$-prostaglandin $I_1$
(81) 18,19-tetrahydro-17-methyl-20-propyl-9(O)-methano-$\Delta^{6(9\alpha)}$-prostaglandin $I_1$
(82) 18,19-tetrahydro-17,20,20-trimethyl-9(O)-methano-$\alpha^{6(9\alpha)}$-prostaglandin $I_1$
(83) 18,19-tetrahydro-17,20,20,20-tetramethyl-9(O)-methano-$\Delta^{6(9\alpha)}$-prostaglandin $I_1$
(84) 18,19-tetrahydro-17,20-dimethyl-20-ethyl-9(O)-methano-$\Delta^{6(9\alpha)}$-prostaglandin $I_1$
(85) 18,19-tetrahydro-17,20,20-trimethyl-20-ethyl-9(O)-methano-$\Delta^{6(9\alpha)}$-prostaglandin $I_1$
(86) 18,19-tetrahydro-17-methyl-20,20-diethyl-9(O)-methano-$\Delta^{6(9\alpha)}$-prostaglandin $I_1$
(87) 18,19-tetrahydro-17-methyl-20-isopropyl-9(O)-methano-$\Delta^{6(9\alpha)}$-prostaglandin $I_1$
(88) 18,19-tetrahydro-17-methyl-20-t-butyl-9(O)-methano-$\Delta^{6(9\alpha)}$-prostaglandin $I_1$
(89) 18,19-tetrahydro-17,20-dimethyl-20-propyl-9(O)-methano-$\Delta^{6(9\alpha)}$-prostaglandin $I_1$
(90) 18,19-tetrahydro-17,20,20-trimethyl-20-propyl-9(O)-methano-$\Delta^{6(9\alpha)}$-prostaglandin $I_1$
(91) 18,19-tetrahydro-17-methyl-20-(2-methylpropyl)-9(O)-methano-$\Delta^{6(9\alpha)}$-prostaglandin $I_1$
(92) 18,19-tetrahydro-17-methyl-20-(2,2-dimethylpropyl)-9(O)-methano-$\Delta^{6(9\alpha)}$-prostaglandin $I_1$
(93) 18,19-tetrahydro-17,20-dimethyl-20-butyl-9(O)-methano-$\Delta^{6(9\alpha)}$-prostaglandin $I_1$
(94) 18,19-tetrahydro-17,20,20-trimethyl-20-butyl-9(O)-methano-$\Delta^{6(9\alpha)}$-prostaglandin $I_1$
(95) 18,19-tetrahydro-17-methyl-20-(2-methylbutyl)-9(O)-methano-$\Delta^{6(9\alpha)}$-prostaglandin $I_1$
(96) 18,19-tetrahydro-17-methyl-20-(2-ethylbutyl)-9(O)-methano-$\Delta^{6(9\alpha)}$-prostaglandin $I_1$
(97) 18,19-tetrahydro-17-methyl-20-(2,2-dimethylbutyl)-9(O)-methano-$\Delta^{6(9\alpha)}$-prostaglandin
(98) 19,20-tetrahydro-17-methyl-9(O)-methano-$\Delta^{6(9\alpha)}$-prostaglandin $I_1$
(99) 19,20-tetrahydro-17,18-dimethyl-9(O)-methano-$\Delta^{6(9\alpha)}$-prostaglandin $I_1$
(100) 19,20-tetrahydro-17,18,20-trimethyl-9(O)-methano-$\Delta^{6(9\alpha)}$-prostaglandin $I_1$
(101) 19,20-tetrahydro-17,20-dimethyl-9(O)-methano-$\Delta^{6(9\alpha)}$-prostaglandin $I_1$
(102) 19,20-tetrahydro-17-methyl-20-ethyl-9(O)-methano-$\Delta^{6(9\alpha)}$-prostaglandin $I_1$
(103) 19,20-tetrahydro-17-methyl-20-isopropyl-9(O)-methano-$\Delta^{6(9\alpha)}$-prostaglandin $I_1$
(104) 19,20-tetrahydro-17-methyl-20-t-butyl-9(O)-methano-$\Delta^{6(9\alpha)}$-prostaglandin $I_1$
(105) 19,20-tetrahydro-17-methyl-20-propyl-9(O)-methano-$\Delta^{6(9\alpha)}$-prostaglandin $I_1$
(106) 19,20-tetrahydro-17-methyl-20-(1-methylpropyl)-9(O)-methano-$\Delta^{6(9\alpha)}$-prostaglandin $I_1$
(107) 19,20-tetrahydro-17-methyl-20-(1-ethylpropyl)-9(O)-methano-$\Delta^{6(9\alpha)}$-prostaglandin $I_1$
(108) 19,20-tetrahydro-17-methyl-20-(1,1-dimethylpropyl)-9(O)-methano-$\Delta^{6(9\alpha)}$-prostaglandin $I_1$
(109) 19,20-tetrahydro-17-methyl-20-butyl-9(O)-methano-$\Delta^{6(9\alpha)}$-prostaglandin $I_1$
(110) 19,20-tetrahydro-17,18-dimethyl-20-butyl-9(O)-methano-$\Delta^{6(9\alpha)}$-prostaglandin $I_1$
(111) 19,20-tetrahydro-17-methyl-20-(1-methylbutyl)-9(O)-methano-$\Delta^{6(9\alpha)}$-prostaglandin $I_1$
(112) 19,20-tetrahydro-17-methyl-20-(1,1-dimethylbutyl)-9(O)-methano-$\Delta^{6(9\alpha)}$-prostaglandin $I_1$
(113) 19,20-tetrahydro-17-methyl-20-(2,2-dimethylbutyl)-9(O)-methano-$\Delta^{6(9\alpha)}$-prostaglandin $I_1$
(114) 19,20-tetrahydro-17-methyl-20-(2-ethylbutyl)-9(O)-methano-$\Delta^{6(9\alpha)}$-prostaglandin $I_1$
(115) 19,20-tetrahydro-17,18-dimethyl-20-propyl-9(O)-methano-$\Delta^{6(9\alpha)}$-prostaglandin $I_1$
(116) 20-methylidene-17-methyl-9(O)-methano-$\Delta^{6(9\alpha)}$-prostaglandin $I_1$
(117) 20-methylidene-17,18-dimethyl-9(O)-methano-$\Delta^{6(9\alpha)}$-prostaglandin $I_1$
(118) 20-methylidene-17,20-dimethyl-9(O)-methano-$\Delta^{6(9\alpha)}$-prostaglandin $I_1$
(119) 20-ethylidene-17-methyl-9(O)-methano-$\Delta^{6(9\alpha)}$-prostaglandin $I_1$
(120) 20-propylidene-17-methyl-9(O)-methano-$\Delta^{6(9\alpha)}$-prostaglandin $I_1$
(121) 20-(2-methylpropylidine)-17-methyl-9(O)-methano-$\Delta^{6(9\alpha)}$-prostaglandin $I_1$
(122) 20-propylidine-17,19-dimethyl-9(O)-methano-$\Delta^{6(9\alpha)}$-prostaglandin $I_1$
(123) 20-(2,2-dimethylpropylidine)-17-methyl-9(O)-methano-$\Delta^{6(9\alpha)}$-prostaglandin $I_1$
(124) 20-propylidine-17,19,19-trimethyl-9(O)-methano-$\Delta^{6(9\alpha)}$-prostaglandin $I_1$
(125) 20-butylidine-17-methyl-9(O)-methano-$\Delta^{6(9\alpha)}$-prostaglandin $I_1$
(126) 20-butylidine-17,18-dimethyl-9(O)-methano-$\Delta^{6(9\alpha)}$-prostaglandin $I_1$ (127) 20-butylidine-17,18,18-trimethyl-9(O)-methano-$\Delta^{6(9\alpha)}$-prostaglandin $I_1$
(128) 20-butylidine-17,18,18-trimethyl-9(O)-methano-$\Delta^{6(9\alpha)}$-prostaglandin $I_1$
(129) 20-butylidine-17,19,19-trimethyl-9(O)-methano-$\Delta^{6(9\alpha)}$-prostaglandin $I_1$
(130) 20-butylidine-17,19-dimethyl-9(O)-methano-$\Delta^{6(9\alpha)}$-prostaglandin $I_1$
(131) 20-(2-methylbutylidine)-17-methyl-9(O)-methano-$\Delta^{6(9\alpha)}$-prostaglandin $I_1$
(132) 20-(2-ethylbutylidine)-17-methyl-9(O)-methano-$\Delta^{6(9\alpha)}$-prostaglandin $I_1$
(133) 20-(3-methylbutylidine)-17-methyl-9(O)-methano-$\Delta^{6(9\alpha)}$-prostaglandin $I_1$
(134) 20-(3,3-dimethylbutylidine)-17-methyl-9(O)-methano-$\Delta^{6(9\alpha)}$-prostaglandin $I_1$
(135) 20-(3,3-dimethylbutylidine)-17-methyl-9(O)-methano-$\Delta^{6(9\alpha)}$-prostaglandin $I_1$
(136) 20-ethynyl-17-methyl-9(O)-methano-$\Delta^{6(9\alpha)}$-prostaglandin $I_1$
(137) 20-ethynyl-17,18-dimethyl-9(O)-methano-$\Delta^{6(9\alpha)}$-prostaglandin $I_1$
(138) 20-ethynyl-17,19-dimethyl-9(O)-methano-$\Delta^{6(9\alpha)}$-prostaglandin $I_1$
(139) 20-ethynyl-17,19,19-trimethyl-9(O)-methano-$\Delta^{6(9\alpha)}$-prostaglandin $I_1$
(140) 20-ethynyl-17,20-dimethyl-9(O)-methano-$\Delta^{6(9\alpha)}$-prostaglandin $I_1$
(141) 20-ethynyl-17,20,20-trimethyl-9(O)-methano-$\Delta^{6(9\alpha)}$-prostaglandin $I_1$
(142) 20-(1-propynyl)-17-methyl-9(O)-methano-$\Delta^{6(9\alpha)}$-prostaglandin $I_1$
(143) 20-(1-propynyl)-17,18-dimethyl-9(O)-methano-$\Delta^{6(9\alpha)}$-prostaglandin $I_1$
(144) 20-(1-propynyl)-17,19-dimethyl-9(O)-methano-$\Delta^{6(9\alpha)}$-prostaglandin $I_1$
(145) 20-(1-propynyl)-17,19,19-trimethyl-9(O)-methano-$\Delta^{6(9\alpha)}$-prostaglandin $I_1$
(146) 20-(1-propynyl)-17,20-dimethyl-9(O)-methano-$\Delta^{6(9\alpha)}$-prostaglandin $I_1$
(147) 20-(1-propynyl)-17,20,20-trimethyl-9(O)-methano-$\Delta^{6(9\alpha)}$-prostaglandin $I_1$
(148) 20-(1-butynyl)-17-methyl-9(O)-methano-$\Delta^{6(9\alpha)}$-prostaglandin $I_1$
(149) 20-(1-butynyl)-17,18-dimethyl-9(O)-methano-$\Delta^{6(9\alpha)}$-prostaglandin $I_1$
(150) 20-(1-butynyl)-17,19-dimethyl-9(O)-methano-$\Delta^{6(9\alpha)}$-prostaglandin $I_1$
(151) 20-(1-butynyl)-17,19,19-trimethyl-9(O)-methano-$\Delta^{6(9\alpha)}$-prostaglandin $I_1$
(152) 20-(1-butynyl)-17,20-dimethyl-9(O)-methano-$\Delta^{6(9\alpha)}$-prostaglandin $I_1$
(153) 20-(3-methyl-1-butynyl)-17-methyl-9(O)-methano-$\Delta^{6(9\alpha)}$-prostaglandin $I_1$
(154) 20-(3,3-dimethyl-1-butynyl)-17-methyl-9(O)-methano-$\Delta^{6(9\alpha)}$-prostaglandin $I_1$
(155) 20-(2-butynyl)-17-methyl-9(O)-methano-$\Delta^{6(9\alpha)}$-prostaglandin $I_1$
(156) 20-(2-propynyl)-17,18-dimethyl-9(O)-methano-$\Delta^{6(9\alpha)}$-prostaglandin $I_1$
(157) 20-(2-propynyl)-17,18,18-trimethyl-9(O)-methano-$\Delta^{6(9\alpha)}$-prostaglandin $I_1$
(158) 20-(2-propynyl)-17,19-dimethyl-9(O)-methano-$\Delta^{6(9\alpha)}$-prostaglandin $I_1$
(159) 20-(2-propynyl)-17,19,19-trimethyl-9(O)-methano-$\Delta^{6(9\alpha)}$-prostaglandin $I_1$
(160) 20-(2-propynyl)-17,20-dimethyl-9(O)-methano-$\Delta^{6(9\alpha)}$-prostaglandin $I_1$
(161) 20-(1-methyl-2-propynyl)-17-methyl-9(O)-methano-$\Delta^{6(9\alpha)}$-prostaglandin $I_1$
(162) 20-(1,1-dimethyl-2-propynyl)-17-methyl-9(O)-methano-$\Delta^{6(9\alpha)}$-prostaglandin $I_1$
(163) 20-(2-butynyl)-17-methyl-9(O)-methano-$\Delta^{6(9\alpha)}$-prostaglandin $I_1$
(164) 20-(2-butynyl)-17,18-dimethyl-9(O)-methano-$\Delta^{6(9\alpha)}$-prostaglandin $I_1$
(165) 20-(2-butynyl)-17,18,18-trimethyl-9(O)-methano-$\Delta^{6(9\alpha)}$-prostaglandin $I_1$
(166) 20-(2-butynyl)-17,19,19-trimethyl-9(O)-methano-$\Delta^{6(9\alpha)}$-prostaglandin $I_1$
(167) 20-(2-butynyl)-17,20,20-trimethyl-9(O)-methano-$\Delta^{6(9\alpha)}$-prostaglandin $I_1$
(168) 20-(1-methyl-2-butynyl)-17-methyl-9(O)-methano-$\Delta^{6(9\alpha)}$-prostaglandin $I_1$
(169) 20-(1,1-dimethyl-2-butynyl)-17-methyl-9(O)-methano-$\Delta^{6(9\alpha)}$-prostaglandin $I_1$
(170) 20-(3-butynyl)-17-methyl-9(O)-methano-$\Delta^{6(9\alpha)}$-prostaglandin $I_1$
(171) 20-(3-butynyl)-17,18-dimethyl-9(O)-methano-$\Delta^{6(9\alpha)}$-prostaglandin $I_1$
(172) 20-(3-butynyl)-17,18,18-trimethyl-9(O)-methano-$\Delta^{6(9\alpha)}$-prostaglandin $I_1$
(173) 20-(3-butynyl)-17,20-dimethyl-9(O)-methano-$\Delta^{6(9\alpha)}$-prostaglandin $I_1$
(174) 20-(1-methyl-3-butynyl)-17-methyl-9(O)-methano-$\Delta^{6(9\alpha)}$-prostaglandin $I_1$
(175) 20-(2-methyl-3-butynyl)-17-methyl-9(O)-methano-$\Delta^{6(9\alpha)}$-prostaglandin $I_1$
(176) 20-(2,2-dimethyl-3-butynyl)-17-methyl-9(O)-methano-$\Delta^{6(9\alpha)}$-prostaglandin $I_1$
(177) 20-(1,1-dimethyl-3-butynyl)-17-methyl-9(O)-methano-$\Delta^{6(9\alpha)}$-prostaglandin $I_1$
(178) An ethyl ester of (1) to (177)
(179) A butyl ester of (1) to (177)
(180) A sodium salt of (1) to (177)
(181) A potassium salt of (1) to (177)
(182) An ammonium salt of (1) to (177)
(183) (1) to (182) where the methyl group of the 17-position is an ethyl group but the invention is not limited to the same.

The isocarbacyclin of the above formula (I) is easily produced by known methods. These processes of production are described in, for example, Japanese Unexamined Patent Publication (Kokai) Nos. 59-210044, 61-197518, etc.

It became clear that there was a powerful skin ulcer treatment activity upon use of the isocarbacyclin of the formula (I) as an external skin treatment agent composition, in particular, a transdermal agent. For example, application of an ointment containing isocarbacyclin of formula (I) to a diseased location, that is, a skin ulcer (rabbit decubitus ulcer lesion model) prepared by applying pressure to the skin on the back of a rabbit, exhibited a therapeutic effect. Further, the isocarbacyclin of the formula (I) exhibited a tendency to reduce the number of days for complete curing of a scald (ulcer surface) in a rat scalding model. In addition, an ointment containing the isocarbacyclin of formula (I) remarkably increased the amount of the blood flow of the skin at the site of application in hairless rats.

The above active compound may be used as an external skin treatment agent, in particular, an agent for treatment of skin ulcers, for example, decubitus ulcers, scald ulcers, diabetic ulcers, peripheral circulatory disorders, ulcers accompanying collagen diseases, and other ulcers.

As the preparation of the transdermal agent composition having, as an active ingredient, the isocarbacyclin of the formula (I), mention may be made of an ointment, cream, lotion, liquid, etc.

As the carrier (base) of the external skin treatment agent of the present invention, mention may be made, for example, of castor oil, olive oil, sesame oil, safflower oil, and other fatty oils, lanolin, white, yellow, or hydrophilic vaselin, beeswax, bleached beeswax, spermaceti wax, paraffin wax, and other waxes, oleyl alcohol, isostearyl alcohol, octyl dodeca alcohol, hexyl decanol, and other higher alcohols, glycerin, diglycerin, ethylene glycerol, propylene glycol, sorbitol, 1,3-butanediol, and other glycols. Further, as the solubilizing agent of the prostacyclin, use may be made of ethanol, dimethylsulfoxide, polyethylene glycol, etc. Also, in accordance with need, use may also be made of antioxidants such as paraoxyl benzoic acid esters, sodium benzoate, salicylic acid, sorbic acid, boric acid, and other preservatives, dibutylhydroxytoluene, and the like. In addition, suitable amounts of oil components, surfactants, water, moisture retainers, thickeners, fragrances, dyes, etc. may be added to an extent not impairing the effect of the present invention.

The concentration of the active ingredient in the external skin treatment agent composition according to the present invention is not particularly limited, but preferably is $10^{-6}$ to $10^{-1}$% by weight, more preferably $10^{-5}$ to $10^{-2}$% by weight, in terms of the total composition.

To promote the transdermal absorption of isocarbacyclin, an absorption promotor such as diisopropyl adipate, diethyl sebacate, ethyl caproate, ethyl laurate, etc. may be added.

An ointment may be produced by an ordinary method. For example, mention may be made of the method of adding a fatty oil to an isocarbacyclin, dissolving the same in it, adding this solution to a separately warmed and melted wax, homogeneously mixing them, and then cooling.

A cream can be produced by an ordinary method. For example, mention may be made of the method of heating and melting an isocarbacyclin and an oil phase component (fatty oil, surfactant), adding heated water to this, adding a mixture of glycols, while stirring, and then cooling.

Aside from these preparations, mention may be made of preparations such as lotions, liquids, pastes, cataplasms, and aerosols. The preparations may be produced by ordinary methods.

The dosage of the isocarbacyclin differs depending on the type of the compound, the state of the disease, etc., but the medication is usually administered in an amount of from about 1 ng to about 1 mg/site. Accordingly, the amount of the isocarbacyclin contained in the transdermal medication is determined by the dosage.

The transdermal medication having an isocarbacyclin as an active ingredient according to the present invention, as mentioned earlier, is applied locally to the skin, so is limited in location of action and therefore can exhibit a pharmacological activity just at a specific site.

According to the present invention, it is clear that isocarbacyclin of the formula (I) exhibits a therapeutic effect on skin ulcers. Note that the external skin ointment of the present invention was not observed to particularly have acute toxicity.

EXAMPLES

The present invention will be explained in further detail by Examples.

EXAMPLE 1

One hundred grams of an ointment having the following composition were prepared.

| | |
|---|---|
| 17(S),20-dimethyl-9-(O)-methano-$\Delta^{6(9\alpha)}$-prostaglandin $I_1$ | 0.05 mg |
| Beeswax | 33 g |
| Vegetable oil | 67 g |

EXAMPLE 2

One hundred grams of a cream having the following composition were prepared.

| | |
|---|---|
| 17(S),20-dimethyl-9-(O)-methano-$\Delta^{6(9\alpha)}$-prostaglandin $I_1$ | 0.05 mg |
| Beeswax | 10 g |
| Paraffin wax | 6 g |
| Lanolin | 3 g |
| Isopropyl myristate | 6 g |
| Squalane | 8 g |
| Liquid paraffin | 25 g |
| Sorbitan monostearate | 4 g |
| Polyoxyethylenesorbitan monostearate | 2 g |
| Preservative | q.s. |
| Propylene glycol | 2 g |
| Water | 34 g |

EXAMPLE 3

Transdermal therapeutic effect on skin ulcers by 17(S),20-dimethyl-9(O)-methano-$\Delta^{6(9\alpha)}$-prostaglandin $I_1$ Coating an ointment containing 17(S),20-dimethyl-9-(O)-methano-$\Delta^{6(9\alpha)}$-prostaglandin $I_1$ to a skin ulcer (rabbit decubitus ulcer lesion model) prepared by applying pressure to the skin on the back of a rabbit exhibited a therapeutic effect. That is, the skin areas on the III trochanters on the left and right of Japanese white male rabbits fasted for 15 to 20 days were dipilated and pressure was applied on those portions to prepare skin ulcers. Subsequently, an ointment containing prostacyclin was coated on the right lesions of the subjects and vaseline on the left lesions once a day in amounts of 0.02 g/site. The curing process of the lesions was found by the ratio of area by the following equation in accordance with the method of Fukawa ("Applied Pharmacology", 7, 1305, 1973).

Ratio of area (%)=(long length×short length of ulcer area) (day observed)/(long length×short length of ulcer area) (day ulcer prepared)×100.

The results are shown in Table 1. The lesions coated with the ointment containing the isocarbacyclin of the formula (I) shrank significantly compared with the control sites on day 5, and 7 and a therapeutic effect was confirmed.

TABLE 1

| Concentration | Ratio of area of wound (%) | | | | |
|---|---|---|---|---|---|
| | 0 | 3 | 5 | 7 | 10 days |
| 0.0064 µg/g R[a)] | 100 | 104.91 ± 10.58 | 81.40 ± 10.22 | 41.47 ± 8.42 | 20.26 ± 8.69 |
| L[b)] | (N = 12) | (N = 12) | (N = 12) | (N = 12) | (N = 12) |
| | 100 | 103.47 ± 15.65 | 80.79 ± 15.33 | 51.97 ± 11.97 | 20.14 ± 6.91 |
| 0.032 µg/g R[a)] | 100 | 78.93 ± 10.28 | 45.76 ± 5.52 | 26.87 ± 4.11* | 9.10 ± 3.06 |
| L[b)] | (N = 12) | (N = 12) | (N = 12) | (N = 12) | (N = 12) |
| | 100 | 101.16 ± 12.93 | 65.65 ± 8.98 | 42.10 ± 5.25 | 17.43 ± 4.45 |
| 0.16 µg/g R[a)] | 100 | 70.03 ± 11.32 | 45.02 ± 7.82* | 25.12 ± 4.74* | 13.38 ± 4.84 |
| L[b)] | (N = 12) | (N = 12) | (N = 12) | (N = 12) | (N = 12) |
| | 100 | 99.87 ± 12.91 | 81.88 ± 11.18 | 49.11 ± 8.91 | 25.40 ± 7.09 |

Figures of ratio of area of wound are mean values ± standard error.
N: Number of animals used
[a)]Right Side: specimen applied
[b)]Left side (control): vaseline applied
*5% significance in comparison with left side (control)

EXAMPLE 4

Transdermal therapeutic effect on scalds by 17(S),20-dimethyl-9(O)-methano-$\Delta^{6(9\alpha)}$-prostaglandin $I_1$ Scalds were prepared by depilating the skin on the backs of male Wistar rats and bringing the skin into contact with the front end of a scald test apparatus heated to 200° C. for 20 seconds. On day 2 after the preparation of the scalds, the dead skin was surgically removed and application of an ointment containing 17(S),20-dimethyl-9(O)-methano-$\Delta^{6(9\alpha)}$-prostaglandin $I_1$ to the lesion sites was started. The scalded portions were observed with the naked eye and the number of days required until the epidermis finished being formed was used as the number of days for a complete cure. The number of days of administration were calculated using the day of the start of the administration as day 0. The ratio of area of the wounds was found by the following equation.

Ratio of area (%)=(long length×short length of ulcer area) (day observed)/(long length×short length of ulcer area) (day administration started)×100.

Figure 2:
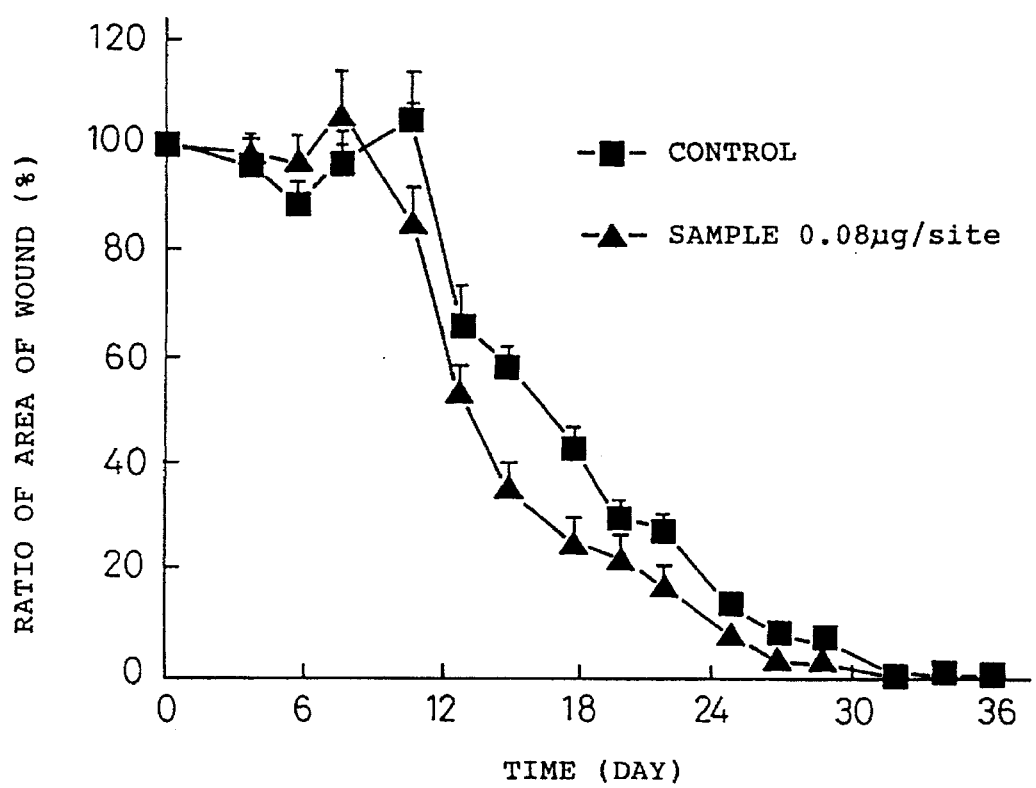
FIG. 2 is a graph of the results of an evaluation of the pharmacological effect of an external skin treatment agent composition of the present invention display changes with time in ratio of area of wound (n=11 to 12, Average ±SE)

As a result, as shown in Table 2 and. FIG. 1 and FIG. 2, a trend was observed of a faster cure with a high dosage (0.08 µg/site) judging from the number of days for a complete cure and the ratio of area of the wounds.

TABLE 2

Evaluation of Pharmacological Effect of Ointment Using Rat Scalding Model (Number of Days for Complete Cure)

| Tested group | No. of days for complete cure (days) Average ± S.E. |
|---|---|
| Control group Sample administered group: | 35  32  34  29  25  32  28  34  32  26  26  —   30.3  1.0 |
| 0.08 µg/site/day | 28  20  32  27  29  25  28  25  32  32  29  21   27.3  1.1 |

EXAMPLE 5

Transdermal action of increasing amount of blood flow of skin by 17(S),20-dimethyl-9(O)-methano-$\Delta^{6(9\alpha)}$-prostaglandin $I_1$ An ointment containing 17(S),20-dimethyl-9(O)-methano-$\Delta^{6(9\alpha)}$-prostaglandin $I_1$ remarkably increased the amount of the blood flow of the skin at the sites of administration of hairless rats as shown in FIG. 3.

The external skin treatment agent composition having the isocarbacyclin of formula (I) according to the present invention as its active ingredient exhibited a superior therapeutic effect.

We claim:

1. A method of treating an ulcer selected from the group consisting of decubitus ulcers, scald ulcers, diabetic ulcers, peripheral circulatory disorders, and ulcers accompanying collagen diseases, said method the step of comprising administering a topically effective amount of a composition containing an active ingredient comprising an isocarbacyclin, and/or an optical isomer thereof, of the formula (I) to a mammal in need of such treatment:

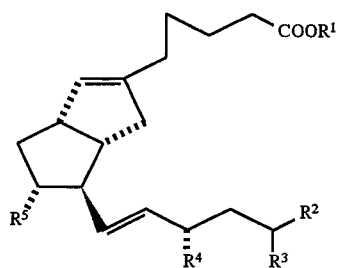

wherein $R^1$ is a hydrogen atom, a straight chain or branched alkyl group of $C_1$ to $C_{10}$ or one equivalent of a cation; $R^2$ is a substituted or unsubstituted $C_1$ to $C_{10}$ straight chain or branched alkyl group or substituted or unsubstituted $C_2$ to $C_{10}$ straight chain or branched alkenyl group or alkynyl group; $R^3$ is a straight chain alkyl group of $C_1$ to $C_5$; and $R^4$ and $R^5$ are independently a hydroxyl group or a group of the formula:

wherein $R^6$ is a $C_1$ to $C_5$ straight chain or branched alkyl group and a carrier.

2. The method as claimed in claim 1, wherein $R^1$ in formula (I) is a hydrogen atom or a methyl group.

3. The method as claimed in claim 1, wherein $R^2$ in formula (I) is a butyl group.

4. The method as claimed in claim 3, wherein $R^3$ in formula (I) is a methyl group.

5. The method as claimed in claim 4, wherein the composition is a transdermal composition.

* * * * *